US010806601B2

(12) United States Patent
Bonnet et al.

(10) Patent No.: US 10,806,601 B2
(45) Date of Patent: Oct. 20, 2020

(54) METHOD FOR REGULATING A PROSTHESIS CONTROLLED BY A MICROCONTROLLER, AND PROSTHESIS EQUIPPED WITH A MICROCONTROLLER FOR IMPLEMENTATION OF THE REGULATING METHOD

(71) Applicant: Proteor, Saint-apollinaire (FR)

(72) Inventors: Xavier Bonnet, Dijon (FR); Francis Djian, Genlis (FR)

(73) Assignee: Proteor, Saint-apollinaire (FR)

( * ) Notice: Subject to any disclaimer, the term of this patent is extended or adjusted under 35 U.S.C. 154(b) by 173 days.

(21) Appl. No.: 15/574,495

(22) PCT Filed: May 17, 2016

(86) PCT No.: PCT/FR2016/051161
§ 371 (c)(1),
(2) Date: Nov. 16, 2017

(87) PCT Pub. No.: WO2016/185132
PCT Pub. Date: Nov. 24, 2016

(65) Prior Publication Data
US 2018/0133031 A1 May 17, 2018

(30) Foreign Application Priority Data
May 19, 2015 (FR) ...................... 15 54477

(51) Int. Cl.
*A61F 2/60* (2006.01)
*A61F 2/64* (2006.01)
(Continued)

(52) U.S. Cl.
CPC .................. *A61F 2/60* (2013.01); *A61F 2/64* (2013.01); *A61F 2/66* (2013.01); *A61F 2/6607* (2013.01);
(Continued)

(58) Field of Classification Search
CPC ...... A61F 2/64; A61F 2/68; A61F 2002/6854; A61F 2002/704; A61F 2002/764; A61F 2002/7625
See application file for complete search history.

(56) References Cited

U.S. PATENT DOCUMENTS

| 9,763,809 B2 * | 9/2017 | Palmer .................. A61F 2/6607 |
| 2010/0125229 A1 * | 5/2010 | Rudolph .............. A61B 5/1038 602/16 |

(Continued)

FOREIGN PATENT DOCUMENTS

EP 2842522 3/2015

OTHER PUBLICATIONS

International Search Report and the Written Opinion dated Aug. 1, 2016 from the International Searching Authority Re. Application No. PCT/FR2016/051161.

*Primary Examiner* — Christie L Bahena

(57) ABSTRACT

Method for regulating a prosthesis (1), such as a knee prosthesis, ankle prosthesis or knee/ankle prosthesis, comprising at least one joint (2) controlled by an actuator (3) governed by a microcontroller (4) on the basis of data issuing from at least one gyroscope (5) and an accelerometer (6) that are able to measure the angular speed and the acceleration, respectively, of at least part of the prosthesis (1). According to the invention, the method is such that, during a defined period of time, the microcontroller (4) monitors the measurement given by the gyroscope (5), in such a way that said microcontroller (4) enters an idle state by reducing or by cutting the electrical power of at least one electronic organ of the prosthesis (1), except that of the accelerometer (6), when said microcontroller (4) detects that the absolute value of the measurement given by the gyroscope (5) is below a given threshold during the defined period of time.

7 Claims, 2 Drawing Sheets

(51) Int. Cl.
*A61F 2/66* (2006.01)
*A61F 2/70* (2006.01)
*A61F 2/68* (2006.01)
*A61F 2/76* (2006.01)

(52) U.S. Cl.
CPC .................. *A61F 2/68* (2013.01); *A61F 2/70* (2013.01); *A61F 2002/704* (2013.01); *A61F 2002/764* (2013.01); *A61F 2002/7625* (2013.01)

(56) References Cited

U.S. PATENT DOCUMENTS

| | | | |
|---|---|---|---|
| 2011/0010875 A1* | 1/2011 | Iwahori | A46B 15/0006 15/22.1 |
| 2011/0264238 A1 | 10/2011 | van der Merwe et al. | |
| 2012/0191017 A1* | 7/2012 | Huang | A61F 2/72 600/595 |
| 2013/0261766 A1 | 10/2013 | Langlois et al. | |
| 2015/0182354 A1* | 7/2015 | Bonnet | A61F 2/64 623/26 |

* cited by examiner

METHOD FOR REGULATING A PROSTHESIS CONTROLLED BY A MICROCONTROLLER, AND PROSTHESIS EQUIPPED WITH A MICROCONTROLLER FOR IMPLEMENTATION OF THE REGULATING METHOD

RELATED APPLICATIONS

This application is a National Phase of PCT Patent Application No. PCT/FR2016/051161 having International filing date of May 17, 2016, which claims the benefit of priority of French Patent Application No. 1554477 filed on May 19, 2015. The contents of the above applications are all incorporated by reference as if fully set forth herein in their entirety.

FIELD AND BACKGROUND OF THE INVENTION

The present invention relates to a method for regulating a prosthesis comprising one or several joint(s) controlled by a microcontroller, such as a knee, ankle or knee/ankle prosthesis intended for persons who have had a lower limb amputated, for example. The invention also relates to a prosthesis equipped with a microcontroller for implementing said regulating method.

Prostheses are known from the state of the art that comprise a joint controlled by an actuator whose degree of flexural braking is governed by a microcontroller on the basis of data for example issuing from a gyroscope and an accelerometer capable of respectively measuring the angular speed and the acceleration of at least part of the prosthesis.

Such a type of known prosthesis, for example a knee/ankle femoral prosthesis in particular described in international patent application WO 2014/016424, in the Applicant's name, comprises a hydraulic actuator system arranged to control the knee and ankle joint and the degree of flexural braking of which is governed by at least one valve, in turn governed by a motor. The motor in turn is governed by the microcontroller on the basis of data for example issuing from sensors, for example a gyroscope detecting the angular speed of the tibia relative to the mediolateral axis, an accelerometer measuring the acceleration of the tibia along the anteroposterior axis, a sensor indicating the angle of the knee, and a connecting rod instrumented by a strain gauge making it possible to evaluate the moment of the ankle relative to a mediolateral axis.

Processing the data issuing from the sensors makes it possible to detect different phases of walking and the adaptation of the knee and ankle to various situations from among walking on the level, on a slope, on stairs, sitting-standing transitions, etc.

However, the energy-life (run-time) of this type of prosthesis, which is a crucial factor for the user, depends on the capacity of the on-board battery and the consumption as such, and may be greatly increased.

SUMMARY OF THE INVENTION

One of the aims of the invention is therefore to resolve these drawbacks by proposing a method for regulating a prosthesis making it possible to increase the operating run-time of said prosthesis.

To that end, a method is proposed for regulating a prosthesis comprising at least one joint controlled by an actuator governed by a microcontroller on the basis of data issuing from at least one gyroscope and an accelerometer that are able to measure the angular speed and the acceleration, respectively, of at least part of the prosthesis.

According to the invention, the method consists of the fact that, during a defined period of time, the microcontroller monitors the measurement given by the gyroscope, in such a way that said microcontroller enters an idle state by reducing the electrical power of at least one electronic organ of the prosthesis, except that of the accelerometer, when said microcontroller detects that the absolute value of the measurement given by the gyroscope is below a given threshold during the defined period of time.

Thus, when the gyroscope of the prosthesis is stable, i.e., when it evaluates an absence of movement by the prosthesis, the microcontroller goes to the idle state and the electronic organs of the prosthesis are made idle. Entering into the idle state thus makes it possible to reduce the electricity consumption by reducing the power supply of the electronic organs when they are not being used.

Advantageously, during the defined period of time during which the microcontroller monitors the measurement provided by the gyroscope, the accelerometer calculates and records the average acceleration, such that when the accelerometer detects a defined deviation between the value of the acceleration measured during the idle state and the value of the average acceleration recorded before entering the idle state of the microcontroller, the accelerometer generates a signal able to cause the microcontroller to reenter a normal operating state by reestablishing the normal electricity supply to the electronic organ(s) of the prosthesis.

In this way, the method makes it possible to transition the microcontroller automatically from the idle state to the normal operating state solely because of the accelerometer, which has a relatively low energy consumption. The method therefore makes it possible to reduce or cut the electricity supply only when the prosthesis does not need any electricity supply, and to reenter the normal operating state with a lower electricity supply need. The electricity supply of the prosthesis is therefore managed in real-time, and in a customized manner based on the actual need for electricity by the electronic members. The electricity consumption is optimized, and the run-time is increased accordingly.

Thus, the idle state is exited upon detection of a variation in the average measured acceleration relative to the average acceleration before entering the idle state. In this way, the prosthesis does not reactivate itself inopportunely when it receives a slight jolt. Exiting the idle state is calculated in a relative manner with respect to the environment and situation of the prosthesis before entering the idle state.

The accelerometer is capable of calculating and recording the information itself relative to the acceleration averages, since it has an on board computer. The on board computer in the accelerometer is capable of calculating, autonomously, the averages and the variation between the averages. The accelerometer consumes very little energy, even with the integrated specific computer. During the idle state, the main computer of the prosthesis is also cut, since the accelerometer includes sufficient computing means.

According to one particular embodiment of the regulating method according to the invention, the gyroscope is arranged so as to measure the angular speed of a segment linked to the prosthetic joint with respect to a mediolateral axis, and the accelerometer is arranged so as to measure the acceleration of a segment linked to the prosthetic joint along an anteroposterior axis.

In this configuration, the microcontroller controls, via different actuators, the physical properties of one or several joints of the prosthesis during the gait in different situations, whether during walking or climbing slopes or stairs. This control of the joints can be done based on a state machine. This state machine contains different state related to the phases or moments of the walking cycle (first double bearing, middle of bearing, end of unipodal bearing, pre-oscillation phase, middle of oscillating phase, end of oscillating phase, etc.). The joints of the prosthesis are controlled via motors to control a property of the prosthesis in each of these states (shock absorbing, position of a hydraulic stop, etc.). Different sensors can be used to define the transitions between these different states, for example a sensor indicating the angle of the knee or means making it possible to evaluate the moment of the ankle relative to a mediolateral axis, such as a part instrumented by a strain gauge, for example.

Thus, the microcontroller enters the idle state when it detects, on the one hand, that the measurement given by the gyroscope is below a given threshold for a minimum period of time, and on the other hand, that the prosthesis is in a state making it possible to ensure user safety during the idle state, for example a state in which the resistance of the joint is high, i.e., above a predefined threshold, or in a state in which the joint is blocked.

Thus, if the state machine contains different states, the passage to an idle state is only possible from states where the prosthesis ensures user safety.

In other words, in this configuration, when said microcontroller detects that the measurement given by the gyroscope is below a given threshold for a minimum period of time, this means that the prosthetic segment to which the gyroscope is connected has no rotational movements. Thus, either the prosthetic segment is in pure translation, or it is immobile. In both of these cases, it is no longer useful to try to detect the transition between the states of the state machine, or to try to alter the behavior of the prosthetic joints. It is then possible to place part of the system in an idle state to save energy and increase the operating run-time of the prosthesis.

Preferably, when the microcontroller enters the idle state, it cuts the electrical power of at least one electronic organ, and preferably all of the electronic organs of the prosthesis, with the exception of that of the accelerometer.

Preferably, the signal generated by the accelerometer allows the microcontroller once again to enter the normal operating state, and the system returns to the state of the state machine that the system was in before it entered the idle state.

The invention also relates to a prosthesis, such as a knee, ankle, or knee/ankle prosthesis, comprising at least one joint controlled by an actuator governed by a microcontroller on the basis of data issuing from at least one gyroscope and an accelerometer that are able to measure the angular speed and the acceleration, respectively, of at least part of the prosthesis.

According to the invention, the prosthesis comprises a microcontroller able to monitor, during a defined period of time, the measurement given by the gyroscope and to enter an idle state by reducing or cutting the electrical power of at least one electronic organ of the prosthesis, except that of the accelerometer, when said microcontroller detects that the absolute value of the measurement given by the gyroscope is below a given threshold during the defined period of time.

BRIEF DESCRIPTION OF THE SEVERAL VIEWS OF THE DRAWINGS

Other advantages and features will better emerge from the following description, given as a non-limiting example, of a method for regulating a knee, ankle, or knee/ankle prosthesis according to the invention, in reference to the appended figures, in which.

DESCRIPTION OF SPECIFIC EMBODIMENTS OF THE INVENTION

The invention relates to a method for regulating a prosthesis for placing its electronic organs in an idle state in order to decrease the energy consumption of said prosthesis and increase its operating run-time.

The method according to the invention is applicable to any type of prosthesis or orthosis incorporating electronic organs, for example a knee, ankle, or knee/ankle prosthesis intended for people with an amputated lower limb.

Figure 1:
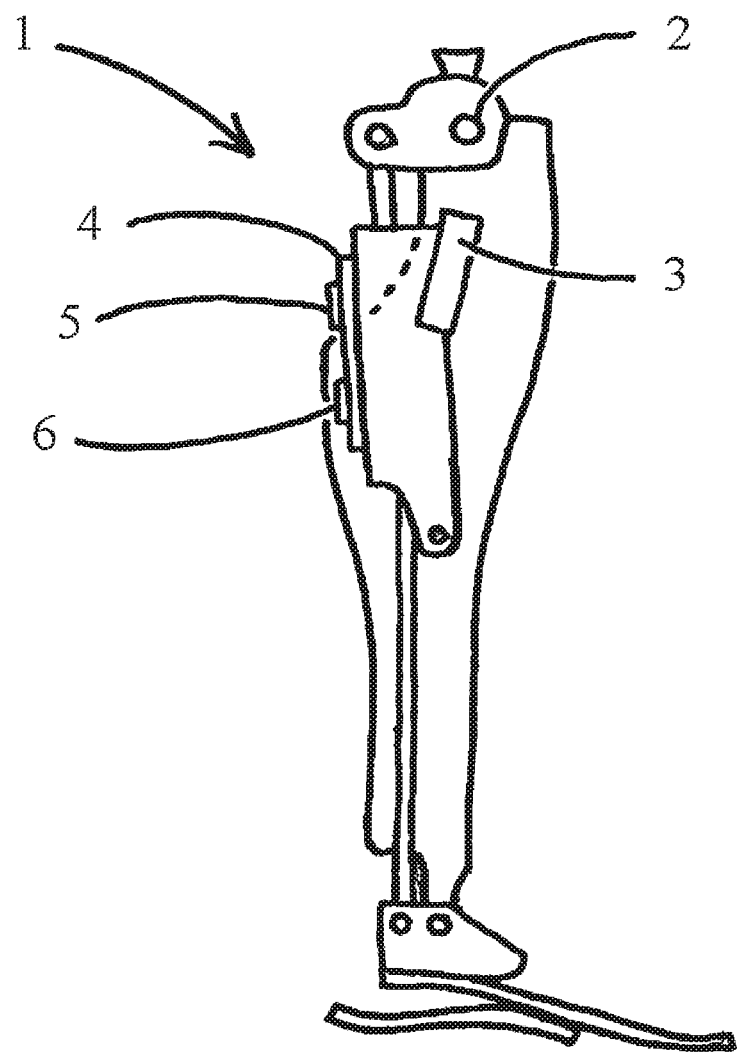
FIG. 1 shows a knee/ankle prosthesis suitable for implementing the control method.

In reference to FIG. 1, the method according to the invention will be described below in relation to a knee/ankle femoral prosthesis (1) comprising a femoral segment capable of being fastened to a femoral connection, and a tibial segment articulated on the one hand to the femoral segment around a joint (2) reproducing the movements of the knee, and on the other hand to a foot around a joint reproducing the movements of the ankle.

The prosthesis (1) for example comprises a hydraulic actuator system (3) arranged to control the joint (2) of the knee and the ankle and the degree of flexural braking of which is governed by a solenoid valve, in turn governed by a motor.

The hydraulic actuator system (3), not shown in detail, for example includes a first double-acting hydraulic jack, the ends of which are respectively secured to the femoral segment and the tibial segment, and a second double-acting jack, the ends of which are respectively secured to the tibial segment and the foot via a connecting rod.

The motor is governed by a microcontroller (4) able to determine the walking phase, such as the bearing phase or the oscillating phase, and the situation, such as descending a set of stairs, a slope, or a standing or similar stance on the basis of data issuing from sensors placed on the knee joint (2) and/or the ankle joint and/or the tibia and/or the jacks.

These sensors are for example a gyroscope (5) detecting the angular speed of the tibia relative to the mediolateral axis, an accelerometer (6) measuring the acceleration of the tibia along the anteroposterior axis, a sensor indicating the angle of the knee, and a connecting rod instrumented by a strain gauge making it possible to evaluate the moment of the ankle relative to a mediolateral axis.

Said microcontroller (4) governs the solenoid valve(s) so as to vary the resistances to flexion or extension of the knee joint (2) and/or the ankle joint. The flexion of the knee for example allows an ankle dorsiflexion proportional to the movement of the knee during the bearing phase and the flexion of the knee causes a dorsiflexion of the ankle during the oscillating phase.

As a function of the walking phase and the situation that are determined by the microcontroller (4), the method according to the invention makes it possible to place said microcontroller (4) in an idle state by reducing or cutting the electrical power of at least one electronic organ of the prosthesis (1), and preferably all of the electronic organs, except that of the accelerometer (6), and thus leaving the actuators (3) in the position that they were in before entering the idle state.

Figure 2:
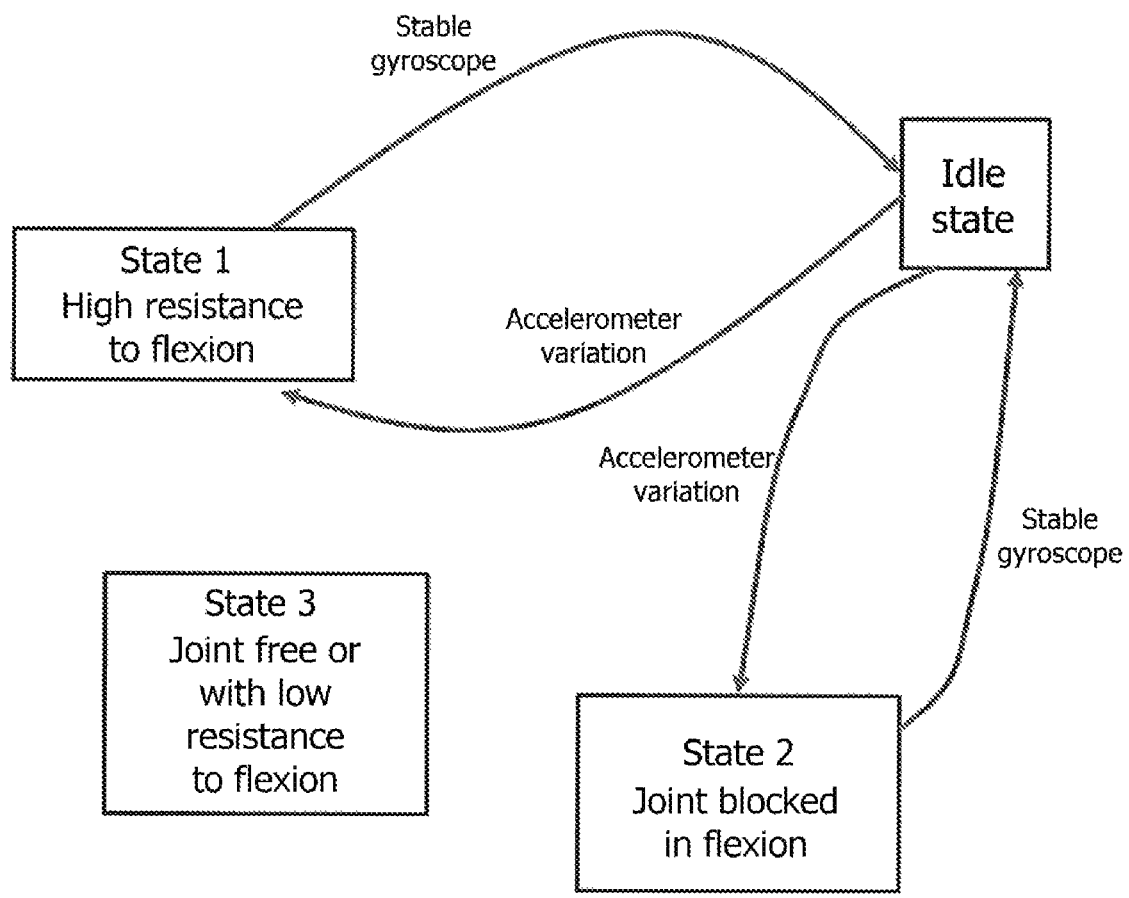
FIG. 2 showing an excerpt from a state machine on which software on board the microcontroller is based.

Indeed, as illustrated in FIG. 2, during a defined period of time, the microcontroller (4) monitors the measurement given by the gyroscope (5), such that said microcontroller (4) enters the idle state when it detects that the gyroscope (5) is stable, i.e., that the absolute value of the measurement given by the gyroscope (5) is below a given threshold during the defined period of time.

The departure from the idle state is done via the accelerometer (6), which detects a variation of the acceleration measured by the accelerometer (6), due either to a jolt on the tibia, or to a change in the angle of the tibia relative to the vertical.

Advantageously, and in reference to FIG. 2, when the microcontroller (4) detects, on the one hand, a state making it possible to ensure user safety during the idle state, such as a state in which the resistance to knee flexure is at a high value making it possible to brake or block the stressed knee, and on the other hand, that the gyroscope (5) is stable, i.e., that the absolute value of the measurement given by the gyroscope (5) is below a given threshold during a defined period of time, said microcontroller (4) enters the idle state in order to save energy and increase the operating run-time of said prosthesis (1) by leaving the resistance to flexure of the knee at a high value. Thus, if the user abruptly changes position or trips, the flexure of the knee is controlled by a high resistance even before the microcontroller (4) leaves the idle state.

When walking on flat terrain, on a slope or on stairs, the states that have a high resistance to the movement of a joint (2) generally correspond to the bearing phase, with the exception of the end of this phase, which in particular corresponds to the phase for initiating the pendular phase.

Another situation for an equipped person corresponds to a bearing phase in which the knee is not in extension and the person is bearing on his prosthesis (1). In this situation, if part of his prosthesis (1) is kept immobile during the defined period of time, this means that the user is deliberately trying to immobilize his joint (2). It is then interesting to increase the resistance to flexure until blocking the movement of the joint (2), for example in the direction of flexure for the knee, before the microcontroller (4) enters the idle state.

The accelerometer (6) can be the only electronic organ that continues to receive power in order to allow the microcontroller (4) to return to its normal operating state. During the defined period of time during which the microcontroller (4) monitors the gyroscope (5), in parallel, the accelerometer (6) calculates and records the average acceleration over this same period of time, such that when the accelerometer (6) detects a defined deviation between the value of the acceleration measured during the idle state and the value of the average acceleration recorded before entering the idle state of the microcontroller (4), the accelerometer (6) generates a signal able to cause the microcontroller (4) to reenter the normal operating state, under conditions corresponding to the state the microcontroller (4) was in before entering the idle state, by reestablishing the normal electricity supply to the electronic organ(s) of the prosthesis (1). The accelerometer (6) has a low energy consumption relative to the other electronic organs. For example, the accelerometer (6) used can be that marketed under the reference "LIS3DH" by the company STMicroelectronics, which incorporates a control logic making it possible to carry out the steps described above. Its typical consumption is 11 μA.

In this way, the accelerometer (6) is capable of calculating and recording the information itself relative to the acceleration averages, since it has an on board computer. The on board computer in the accelerometer (6) is capable of calculating, autonomously, the averages and the variation between the averages. The accelerometer (6) consumes very little energy, even with the integrated specific computer. During the idle state, the main computer of the prosthesis (1) is also cut, since the accelerometer (6) includes sufficient computing means. Thus, the idle state is exited upon detection of a variation in the average measured acceleration relative to the average acceleration before entering the idle state. In this way, the prosthesis (1) does not reactivate itself inopportunely when it receives a slight jolt. The departure from the idle state is calculated in a relative manner with respect to the environment and situation of the prosthesis (1) before entering the idle state.

The method according to the invention therefore makes it possible to regulate entry into the idle state or exiting from the idle state through the joint use of a gyroscope (5) and an accelerometer (6). The gyroscope (5) allows entry into the idle state by evaluating the absence of movement of the prosthesis (1) and the accelerometer (6) allows exiting from the idle state by evaluating the variation in acceleration relative to that at the time of entering into the idle state.

Of course, for proper operation of the method according to the invention and the state machine on which the software on board the microcontroller (4) is based, electronic components should be chosen for the prosthesis (1) having a relatively short wake up time so as not to compromise user safety.

Lastly, it is clear that the examples that have just been given are only specific illustrations and are by no means limiting as concerns the domains of application of the invention. The invention may of course be adapted to other fields, such as robotics.

What is claimed is:

1. A method for regulating a prosthesis, such as a knee, ankle or knee and ankle prosthesis, comprising at least one joint, controlled by an actuator, governed by a microcontroller on the basis of data provided by at least one gyroscope and an accelerometer that measure an angular speed and an acceleration, respectively, of at least part of the prosthesis, characterized in that, during a defined period of time, the microcontroller monitors the measurement given by the gyroscope such that said microcontroller enters an idle state, in which said microcontroller reduces or cuts off the electricity supply for all electronic members of the prosthesis, except for the electricity supply for the accelerometer, wherein said microcontroller enters said idle state when said microcontroller detects that an absolute value of the measurement given by the gyroscope is below a given threshold during the defined period of time.

2. The method for regulating according to claim 1, characterized in that the gyroscope measures the angular speed of a segment linked to the prosthetic joint, relative to a mediolateral axis, the accelerometer measures the acceleration of a segment linked to the prosthetic joint along an anteroposterior axis, and the microcontroller enters the idle state when the prosthesis is in a state in which a resistance of the joint is above a predefined threshold, or in a state in which the joint is blocked.

3. The method for regulating according to claim 2, characterized in that, during the defined period of time, when the accelerometer detects a defined deviation between the value of the acceleration measured during the idle state and a value of an average acceleration recorded before entering the idle state of the microcontroller, the accelerometer generates a signal that causes the microcontroller to reenter a normal operating state by stopping the cutting off or the reduction of the electricity supply to the electronic members of the prosthesis.

4. The method for regulating according to claim 3, characterized in that the signal generated by the accelerometer causes the microcontroller to reenter the normal operating state by reestablishing a electricity supply to the electronic members of the prosthesis.

5. The method for regulating according to claim 1, characterized in that, during the defined period of time, when the accelerometer detects a defined deviation between the value of the acceleration measured during the idle state and a value of an average acceleration recorded before entering the idle state of the microcontroller, the accelerometer generates a signal that causes the microcontroller to reenter a normal operating state by stopping the cutting off or the reduction of the electricity supply to the electronic members of the prosthesis.

6. The method for regulating according to claim 5, characterized in that the signal generated by the accelerometer causes the microcontroller to reenter the normal operating state under conditions corresponding to a state that the microcontroller was in before entering the idle state, by reestablishing an electricity supply to the electronic members of the prosthesis.

7. A prosthesis, such as a knee, ankle or knee and ankle prosthesis, comprising at least one joint, controlled by an actuator, governed by a microcontroller on the basis of data provided by at least one gyroscope and an accelerometer that measure an angular speed and an acceleration, respectively, of at least part of the prosthesis, the prosthesis further comprising a microcontroller that monitors, during a defined period of time, the measurement given by the gyroscope and enters an idle state when said microcontroller detects that an absolute value of the measurement given by the gyroscope is below a given threshold during the defined period of time; wherein said microcontroller reduces or cuts off the electricity supply of all electronic members of the prosthesis when entering said idle state, except for the electricity supply for the accelerometer.

* * * * *